(12) United States Patent
Grandy (10) Patent No.: US 7,347,342 B2
(45) Date of Patent: Mar. 25, 2008

(54) CONTAINER FOR HOLDING STERILE GOODS AND STERILE GOODS DISPENSER

(76) Inventor: Elmar Grandy, Paul-Gerhardt-Allee 68, D-81245 Munich (DE)

( * ) Notice: Subject to any disclaimer, the term of this patent is extended or adjusted under 35 U.S.C. 154(b) by 383 days.

(21) Appl. No.: 10/977,898

(22) Filed: Oct. 29, 2004

(65) Prior Publication Data

US 2005/0115980 A1    Jun. 2, 2005

Related U.S. Application Data

(60) Provisional application No. 60/515,629, filed on Oct. 30, 2003.

(51) Int. Cl.
*B65G 59/00* (2006.01)
*B65H 3/00* (2006.01)
*G07F 11/16* (2006.01)
*G07F 11/00* (2006.01)

(52) U.S. Cl. .................. 221/263; 221/79; 606/189; 607/115

(58) Field of Classification Search .................. 221/88, 221/263, 270, 281, 155, 185, 233, 234, 236, 221/271, 302, 79, 117; 604/241, 239, 61, 604/62; 206/365, 380, 382, 383; 606/189, 606/183; 607/116, 115
See application file for complete search history.

(56) References Cited

U.S. PATENT DOCUMENTS

| | | | | |
|---|---|---|---|---|
| 4,037,590 A | * | 7/1977 | Dohring et al. ............... 601/20 |
| 4,531,938 A | * | 7/1985 | Kaye et al. .................... 604/62 |
| 4,576,591 A | * | 3/1986 | Kaye et al. .................... 604/62 |
| 4,673,387 A | * | 6/1987 | Phillips et al. ................. 604/62 |
| 4,860,937 A | * | 8/1989 | Arnold ......................... 227/147 |
| 4,998,452 A | * | 3/1991 | Blum ......................... 81/57.37 |
| 5,129,914 A | * | 7/1992 | Choi ........................... 606/189 |
| 5,510,266 A | * | 4/1996 | Bonner et al. ................. 436/43 |
| 5,632,410 A | * | 5/1997 | Moulton et al. ............... 221/79 |
| 6,346,094 B2 | * | 2/2002 | West et al. .................... 604/241 |
| 6,399,394 B1 | * | 6/2002 | Dahm et al. ................. 436/180 |
| 6,472,675 B2 | * | 10/2002 | White et al. .............. 250/506.1 |
| 6,475,436 B1 | * | 11/2002 | Schabbach et al. ........... 422/64 |
| 6,532,390 B1 | * | 3/2003 | Chu et al. ..................... 607/116 |
| 6,585,133 B1 | * | 7/2003 | Brouwer ..................... 221/279 |
| 6,616,616 B2 | * | 9/2003 | Fritz et al. ................... 600/583 |
| 6,783,537 B1 | * | 8/2004 | Kuhr et al. .................. 606/182 |
| 7,004,352 B2 | * | 2/2006 | Choi ........................... 221/263 |
| 7,198,606 B2 | * | 4/2007 | Boecker et al. ............. 600/583 |
| 2001/0014792 A1 | | 8/2001 | West et al. |

FOREIGN PATENT DOCUMENTS

DE    200 15 353 U1    1/2001

\* cited by examiner

*Primary Examiner*—Gene O. Crawford
*Assistant Examiner*—Rakesh Kumar
(74) *Attorney, Agent, or Firm*—Caesar, Rivise, Bernstein, Cohen & Pokotilow, Ltd.

(57) ABSTRACT

A container (100) for holding sterile goods (10) is described, including a container body (20) with at least one continuous receiving channel (21) having a cover (30) at least at one end, wherein a pushing ram is displaceably arranged in the receiving channel (21), whose ram length is shorter than the channel length of the receiving channel (21) so that a cavity (23) is formed in the receiving channel (21) to receive the sterile goods (10), which is closed towards the outside by the cover (30). A dispenser for sterile goods is also described which has an actuating device and the container (100).

19 Claims, 4 Drawing Sheets

CONTAINER FOR HOLDING STERILE GOODS AND STERILE GOODS DISPENSER

CROSS-REFERENCE TO RELATED APPLICATIONS

This utility application claims the benefit under 35 U.S.C. §119(e) of Provisional Application Ser. No. 60/515,629 filed on Oct. 30, 2003 entitled CONTAINER AND DISPENSER FOR STERILE GOODS and whose entire disclosure is incorporated by reference herein.

BACKGROUND OF THE INVENTION

1. Field of Invention

The invention relates to a container for holding sterile goods. The invention especially relates to a container for acupuncture needles. The invention further relates to a sterile goods dispenser and methods for supplying sterile goods, such as especially acupuncture needles, using a sterile goods dispenser.

2. Description of Related Art

In numerous areas of medicine, biology and biochemistry, there is an interest in sterile working conditions, for example, during interventions on living tissue, during manipulations or measurements on cells or cell cultures or the like. Frequently used are technical adjuvants, such as, for example, syringes or scalpels, or auxiliary materials such as, for example, implant materials which are stored under sterile conditions in a protective container and are only released immediately during usage.

Blister packs which, for example, consist of a plastic shell mold and a sealing film are frequently used as sterile goods containers. Cannulas for injection or acupuncture needles, for example, are stored sterile in blister packs. Blister packs have the following disadvantages. Firstly, the packaging material can generally only be used once. Undesirable waste packaging is produced. Secondly, the removal of the sterile-packaged material from the blister pack is associated with a high manual effort and the risk of unintentionally damaging or contaminating the sterile goods. Finally, blister packs have an unfavorable ratio of pack size to size of packaged sterile goods. The packing density of the sterile goods cannot easily be increased.

In DE 200 15 353 01 a container for acupuncture needles is described for a manual acupuncture apparatus wherein a plurality of acupuncture needles affixed to a retaining ring are arranged In a sleeve-shaped container. This container certainly allows a plurality of acupuncture needles to be accommodated and allows the needles to be positioned in conjunction with the manual acupuncture apparatus without any manual contact. However, a substantial disadvantage is that the acupuncture needles in the conventional container cannot be stored protected under sterile conditions. In addition, the conventional container is not suitable for supplying individual acupuncture needles for manual positioning.

Known from U.S. 2001/0014792 is a needle magazine for syringe needles which are arranged under sterile conditions in compartments of a magazine body. For use respectively one needle is removed from the magazine with a syringe piston. The conventional magazine has a complicated structure restricted to usage with specially adapted syringes. The needle magazine is unsuitable for supplying differently shaped needles or tools.

The afore-mentioned disadvantages are not only present in the case of containers or dispensers for syringe or acupuncture needles. Rather, they also arise in all other applications where sterile goods are stored reliably protected and are to be supplied with low operating expenditure.

All references cited herein are incorporated herein by reference in their entireties.

OBJECT OF THE INVENTION

The object of the invention is to propose an improved container to hold sterile goods with which the disadvantages of the conventional containers are overcome and which has an extended range of application. The container should especially have improved protection against environmental influences, a simplified structure and simplified manipulability. The container should especially make it possible to achieve dense packing of a plurality of parts to be stored sterile and automated dispensing. Another object of the invention is to provide an improved dispenser for sterile goods, such as for example syringe or acupuncture needles with which the disadvantages of conventional dispensers or magazines are surmounted. The dispenser should especially possess simplified manipulability and high flexibility during adaptation to various tasks. Another object of the invention is to propose an improved method for supplying sterile goods such as, for example, acupuncture or syringe needles with which the disadvantages of conventional applications of sterile goods containers or dispensers are overcome.

BRIEF SUMMARY OF THE INVENTION

Generally, these objects are solved by a container for holding sterile good(s), said container having a container body with at least one continuous receiving channel having a cover at least at one end, and a pushing ram which is displaceably arranged in the receiving channel, wherein a length of the pushing ram is shorter than the channel length of the receiving channel so that a cavity is formed in the receiving channel to receive the sterile good, said cavity being closed towards the outside by the cover; a dispenser comprising said container and an actuating device; and a method for supplying sterile goods with said dispenser.

With regard lo apparatus, the object of the invention is solved according to a first aspect by a container for holding sterile goods with a container body through which extends at least one receiving channel having, at least at one end where the receiving channel opens to the surface of the container body, a cover which forms a sterile barrier against penetration of undesirable contamination from the environment into the receiving channel herein a cavity to receive the sterile goods is formed in the receiving channel between the cover and a displaceable pushing ram.

The use according to the invention of a compact container body with a receiving channel from which the respective sterile goods, e.g. a syringe or acupuncture needle, can be released by displacing the pushing ram, has the following advantages. Firstly, the container body is repeatedly sterilizable and re-usable so that packaging waste is reduced. Furthermore, the sterile embedding in the container takes place with increased safety. The sterile goods in the receiving channel are substantially surrounded by its sterile inner walls from which no contamination transfers to the sterile goods. Towards the outside the sterile goods at the opening of the receiving channel is shielded by the cover which has a reduced area, for example, compared with blister packs so that the risk of unintentional violation of the cover is reduced. The cover which is destructible to release the sterile goods can be formed with reduced thickness with sufficient stability. Another important advantage, is that the sterile goods can be released with one hand so that for the user the other hand is left free to accept the released sterile goods. Finally, the container according to the invention has a universal applicability for various types of objects to be stored sterile (especially apparatus, parts of apparatus or materials). In the receiving channel, which preferably has an elongated, straight shape, the various parts, such as for example, disposable pipettes, sugar test lancets, scalpel knives, cannula needles, acupuncture needles, implant materials and the like can be positioned in a protected fashion and released by displacing the pushing ram.

If, according to a preferred embodiment of the invention, the pushing ram is equipped with another cavity, such as for example with an inner hole, advantages can be obtained for the stable positioning of the sterile goods in the receiving channel and the displacement of the sterile goods with the pushing ram. Part of the sterile goods, such as for example the needle section of an acupuncture needle or a cannula attachment of a syringe or a cutting edge of a surgical tool, can project into the inner hole while the rest of the sterile goods such as for example the needle handle of the acupuncture needle or the shaft of the surgical tool is located in the cavity between the pushing ram and the cover of the receiving channel. Advantageously, a double guidance of the sterile goods is achieved, on the one hand in the receiving channel and on the other hand in the inner hole of the pushing ram so that when the sterile goods are released from the container according to the invention, the sterile goods are held sufficiently stably on the container until the final manual removal or removal by means of an auxiliary device.

According to another preferred embodiment of the invention, the pushing ram is arranged in a form-locking fashion in the receiving channel. Advantageously the risk of undesired contamination reaching the sterile goods from the direction of the pushing ram can thereby be reduced. Additional protection is achieved if, according to another variant of the invention, the back end of the receiving channel is also fitted with a cover.

The cover at the front and, if necessary, at the back side of the container preferably consists of a layer-like material which is manually destructible with the sterile goods by displacement of the pushing ram. In this case, an additional tool for piercing the sterile cover can be dispensed with. Particularly advantageous with regard to the availability of materials for the formation of a sterility barrier is the use of inherently available laminates based on paper andlor plastic film such as for example so-called "medical paper".

The at least one receiving channel in the container body can be formed with various cross-sectional shapes depending on the specific application. For example, a rectangular, elliptical or circular cross-section can be provided. However, for high storage stability and wedge-free displacement of the pushing ram, especially for rod-shaped or cylindrical sterile goods, a circular cross-section is preferred. A cylindrical receiving channel has the additional advantage that the area of the inner wall is minimized for a predefined volume arid sterilization is thereby simplified and the risk of contamination reduced. It is especially preferred if the at least one receiving channel is formed with a channel internal diameter which is at least 1 mm.

An especially preferred application of the container according to the invention consists in accommodating at least one acupuncture needle with a needle handle and a needle section wherein preferably a receiving channel is provided with a circular cross-section and an internal diameter greater than or equal to the external diameter of the needle handle.

For receiving acupuncture needles it is especially advantageous if the inner hole of the pushing ram is set up to receive the needle section. In addition to the aforesaid double guidance, particular protection for the needle tip is advantageously thereby provided, which is generally an important quality feature of the acupuncture needle. For increased stability of the positioning of the acupuncture needle in the receiving channel it can be advantageous if the diameter of the inner hole of the pushing ram is smaller than the external diameter of the needle handle. This avoids the risk that the acupuncture needle slips completely into the pushing ram or sticks in the inner hole of the pushing ram during its displacement. The needle handle forms a support on which the force transmission takes place during the displacement of the pushing ram.

Advantageously, this invention can be applied with so called guide tube acupuncture needles. With these needles, the sterile good is a combination of a protecting guide tube and a needle with a needle handle and a needle section, wherein the needle is fixed at the inner side of the guide tube e.g. with an adhesive joint. With this embodiment, the pushing ram of the container according to the invention is formed by the guide tube. Accordingly, the inner bore of the pushing ram (guide tube) is slightly greater than the needle handle. Using the guide tube acupuncture needles has the advantage that problems with sterility during charging the container are avoided.

With the use of guide tube acupuncture needles, the needle handle is not capable to transmit sufficient force for breaking the cover. Therefore, according to a further embodiment of the invention, the container is provided with a mandrel onto which a force for opening the cover can be transmitted from the pushing ram, i.e. from the guide tube directly.

If the mandrel has a cutting area at its leading end, the opening of the cover from the inner side of the receiving channel can be essentially facilitated. Further advantages with regard to the handling of the container according to the invention result if the mandrel is a hollow component with a continuous inner channel through which the sterile good can be moved through the opened cover to the outside. In this case, the mandrel is necessary for opening the cover only. The sterile good can be taken from the container without separating the mandrel from the container.

According to a further modification of the invention, the mandrel is provided with a protrusion projecting radially outwards, so that a retention of the mandrel in the container can be improved. The protrusion is, e.g., a cifcumferential protrusion or a protrusion projecting to one side only. The protrusion is positioned on the outer surface of the mandrel, preferably with a distance from the leading end of the mandrel and in particular with a distance from the cutting area. This distance is selected such that the protrusion is positioned in the receiving channel under the opened cover in the advanced state of the mandrel. Advantageously, this makes it possible that, when the mandrel is shifted out of the receiving channel for opening the cover, the protrusion and the mandrel are kept bellow the open cover or in a gap between the container body and the cover so that a further movement of the mandrel is avoided.

According to a preferred embodiment of the invention, the mandrel is provided with a jacket at the back side of the mandrel being directed to a sterile good, wherein the jacket provides a rest for the pushing ram. Preferably, the mandrel or at least the jacket has a variable inner diameter, so that during the opening of the cover in a first phase 1he rest is formed by the jacket, while after the opening of the cover the jacket is expanded and the sterile good is completely passed through the jacket. To this end, the jacket consists preferably of an elastically resilient material. With this embodiment of the invention, the receiving channel has a mandrel receptacle with an increased diameter at the end of the receiving channel closed with the cover. In the mandrel receptacle, the diameter of the receiving channel is greater than in the remaining channel. The dimensioning of the mandrel receptacle allows a relaxation of the jacket of the advanced mandrel (or the complete mandrel) as soon as this has opened the cover.

Particular advantages for the most versatile possible application of the container according to the invention for various types of sterile goods, e.g., for various types of acupuncture needles with different handle and needle sizes are achieved if the ram length of the pushing ram is selected such that the slum of the ram length and the maximum length of needle handles of acupuncture needles of practical interest is equal to or less than the channel length of the receiving channel. In this case, with one standard pushing ram the container according to the invention can be suitably used for all types of acupuncture needles of interest in practice.

The displacement of the pushing ram to release the sterile goods advantageously takes place by exerting a driving force from the back of the container body through the receiving channel. For this purpose, according to another variant, the container according to the invention can be equipped with an actuating part to displace the pushing ram. According to a preferred embodiment, the actuating part has an actuating pin whose size is matched to the internal diameter of the receiving channel According to another especially preferred embodiment of the invention, the container body has a plurality of receiving channels. Unlike the aforesaid blister packs, the receiving channels and thus the sterile goods can be arranged with a high density in the container according to the invention. Furthermore, a reservoir is provided with many individual sterile-goods parts, e.g. acupuncture needles which makes it possible to achieve permanent and uniform working with the sterile goods.

If the receiving channels run parallel from a back side of the container body to its front side, advantages can be obtained for a high spatial storage density of the sterile goods.

In general, the container body ban be formed with any volume shape which is adapted to the respective application of the container according to the invention. According to a preferred variant, the container body has the shape of a right circular cylinder. In this case, advantages can be obtained for an especially compact structure, a simplified alignment of the container in a dispenser according to the invention (see below) and a simplified packaging of the sterile goods in the container according to the invention, which can be automated, e.g., on a rotary-cycle table. For a reproducible setting of the container body relative ,to an actuating device, it can be advantageous if the receiving channels are arranged in the container body such that in a given cross-sectional area of the container body the points of intersection of the continuous receiving channels yield a predetermined pattern. When using a cylindrical container body, said points of intersection preferably lie on a plurality of coaxial circles. In this case, the receiving channels are preferably arranged radially in alignment. This means that said points of intersection of radially adjacent neighboring receiving channels with the cross-sectional area considered lie on straight lines which intersect the cylinder axis, According to an alternative variant, the container body has the shape of a cuboid in which the receiving channels are arranged in rows or in matrix form.

Another advantage of the invention is obtained if the cover of the receiving channels on the front sides, and if necessary on the back sides, of the container body is respectively formed of an integral, layer-shaped material. The formation of sterile barriers by applying the cover can thereby be simplified when packaging sterile goods.

With regard to apparatus, the aforesaid object is solved according to another aspect of the invention by providing a dispenser for sterile goods, especially for acupuncture or syringe needles, which has an actuating device to which a container according to the invention is attached and with which the pushing ram can be actuated in the at least one receiving channel. The dispenser according to the invention advantageously forms a compact device with a wide range of application for various types of sterile goods to be stored under germ-free conditions. The dispenser according to the invention can advantageously be operated one-handed.

According to a preferred embodiment of the invention, the actuating device with an actuating pin for displacement of the at least one pushing rim is accommodated in a housing which forms a handle or a wall support of the dispenser according to the invention. According to a preferred variant, the actuating pin is movable with a manually actuatable drive device. Alternatively, an electrically operated drive device can be provided. Particular advantages for a manual actuation, e.g., using a single finger can be obtained if the drive device comprises a feed rod in the housing to which the actuating pin is affixed. If the actuating pin is arranged eccentrically adjustably, different radial operating positions cam advantageously be set. This makes it possible to use a single actuating pin even in containers having a plurality of receiving channels, which for example, are arranged coaxially in a cylindrical container body.

Additional advantages for simplified operation of the dispenser according to the invention can be obtained if the drive device is additionally equipped with an adjusting device for aligning the container according to the invention relative to the actuating pin. For example, the cylindrical container body can be arranged rotatably on the feed rod and aligned respectively adapted to the actuating pin. This alignment is advantageously further simplified if a latching device is provided which adjusts the container body to certain positions which correspond precisely to the positions of the receiving channels in the container body. A systematic release of the sterile goods, e.g., according to the order of the receiving channels is thereby facilitated.

If the housing of the actuating device is formed as a handle which extends parallel to the receiving channels in the container body, advantages can be obtained for single-handed operation of the dispenser. Alternatively, an alignment perpendicular to the receiving channels can be provided which can be advantageous for certain procedures in which several persons use the dispenser for example.

With regard to method, the aforesaid object of the invention is solved by supplying sterile goods, especially acupuncture or syringe needles using the dispenser according to the invention or the container according to the invention by the fact in each case the sterile goods are displaced in the receiving channel by a displacement of the pushing ram until the cover is pierced by the sterile goods and the exposed part of the sterile goods projects him the container body for further use.

Preferably when using acupuncture needles, the sterile goods are pushed out of the receiving channel such that the needle handle is first released, and said handle is then grasped by a doctor for example and can be inserted into the skin of a person to be treated.

BRIEF DESCRIPTION OF SEVERAL VIEWS OF THE DRAWINGS

Further details and advantages of the invention can be seen from the following description of the appended drawings. The invention will be described in conjunction with the following drawings in which like reference numerals designate like elements and wherein.

DETAILED DESCRIPTION OF THE INVENTION

The invention is explained in the following with reference to containers and dispensers for acupuncture needles as an example. It is emphasized that the implementation of the invention is not restricted to this application but is correspondingly possible with other types of sterile goods of interest in medicine, biology and biochemistry, e.g., with syringe needles or medicine capsules.

Figure 1:
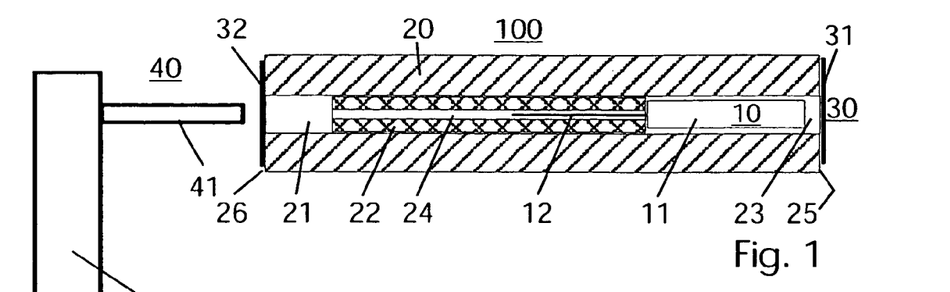
FIGS. 1 and 2 depict a schematic cross-sectional view of a first embodiment of a sterile-goods container according to the invention with a single receiving channel.
Figure 2:
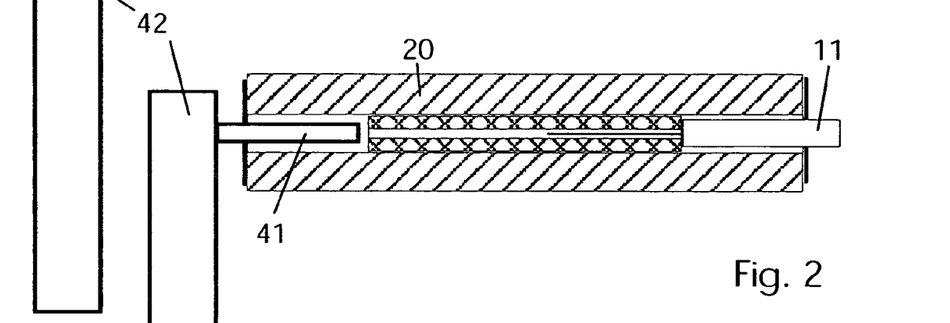

FIGS. 1 and 2 show schematic cross-sectional views of a first embodiment of a container 100 according to the invention in the closed (FIG. 1) and opened (FIG. 2) state. The container 100 for holding the acupuncture needle 10 comprises a container body 20 with a receiving channel 21 and a pushing ram 21 and a cover 30.

The container body 20 consists of a plastic, e.g., polyethylene. It is manufactured, for example, by an injection molding method or as an extruded profile. The external shape of the container body 20 is selected depending on the requirements of the specific application. A cylindrical or cuboid shape can be provided for example. The surface of the container body 20 can advantageously serve as an information carrier. The receiving channel 21 runs as a straight channel from the front side 25 to the back side 26 of the container body 20. At the ends the receiving channel opens into the surface of the container body 20. The pushing ram 22 is arranged displaceably in the receiving channel 21.

The pushing ram 22 has the form of a sleeve or a small lube with an inner hole 24. The external diameter of the pushing ram 22 is equal to the internal diameter of the receiving channel 21. The displaceability of the pushing ram 22 is thereby advantageously ensured without said pushing ram slipping to one side as a result of inertial movements in the receiving channel 21. However, if such slippage is non-critical, the external diameter of the pushing ram can also be smaller than the internal diameter of the receiving channel 21. The pushing ram preferably consists of the same material as the container body 20.

The ram length (axial length) of the pushing ram 22 is smaller than the channel length of the receiving channel 21. A cavity 23 to receive the sterile goods (here: the acupuncture needle) is thereby formed on the front side of the container 100. Depending on the needle size used, a cavity can also remain on the back sidle in the receiving channel.

In the case illustrated, the sterile goods 10 are an acupuncture needle with a needle handle 11 and a needle section 12. The needle section 12 projects into the inner hole 24 of the pushing ram 22.

The cover 30 consists respectively of paper or film covers (31, 32) on the front and back sides 25, 26 of the container body 20. For example, Medical Paper is used. The paper or the film 31, 32 is glued on the container body 20 in an inherently known fashion.

The container body 20 and the receiving channel 21 are dimensioned such that the surface surrounding the exit aperture of the receiving channel 21 on the front and back sides 25, 26 is sufficiently large to achieve a satisfactory blocking effect in conjunction with the cover.

FIGS. 1 and 2 also show an activating part 40 which is adapted to release the acupuncture needle 10 from the container 100. The actuating pan 40 comprises an actuating pin 41 and a handle 42. The length of the actuating pin 41 is selected depending on the dimensions of the container, especially the receiving channel 21 and the pushing ram 22, such that the acupuncture needle 10 can be pushed safely from the receiving channel 21.

FIG. 1 shows the container 100 according to the invention in the closed state. The acupuncture needle 10 is located in a sterile environment in the cavity 23 of the receiving channel 21. In order to release the acupuncture needle 10 the actuating pin 41 is inserted into the back side 26 of the container body 20. The pushing ram 22 is displaced with the actuating pin 41 until the needle handle 11 pierces the coveting film 31 on the front side 25. In this state (FIG. 2) the needle handle 11 projects from the container body 20 so that manual removal and application as directed can be achieved.

The length of the container body 20 is, for example, 70 to 80 mm. The diameter of the receiving channel 21 is, for example, 2.5 mm. The length of the pushing ram 22 is selected such that in the receiving channel 21 the cavity for receiving the usual types of acupuncture needles 10 is sufficiently large. This length is, for example, 50 mm. The blocking area around the exit apertures of the receiving channel has,for example, a radial width of 7 mm. On the back side 26, the container body 20 can be elastically deformable e.g., with a bellow and/or an elastic foil cover, so that even during the operation of the actuating part 40 the back side of the channel 21 remains closed.

Figure 3:
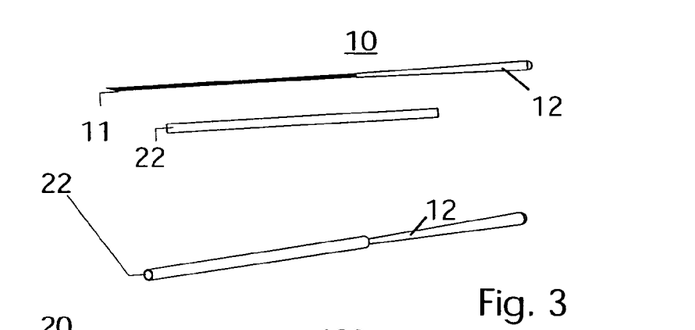
FIG 3. depicts illustrations of a pushing ram used according to the invention in conjunction with an acupuncture needle.

FIG. 3 illustrates the acupuncture needle 10 and the pushing ram 22 as separate parts (above) and when combined (below). The invention advantageously makes it possible to achieve a double guidance of the acupuncture needle 10 in that on the one hand, the needle section 12 is guided in the pushing ram 22 and on the other hand, the pushing ram 22 is guided in the receiving channel 21.

Figure 4:
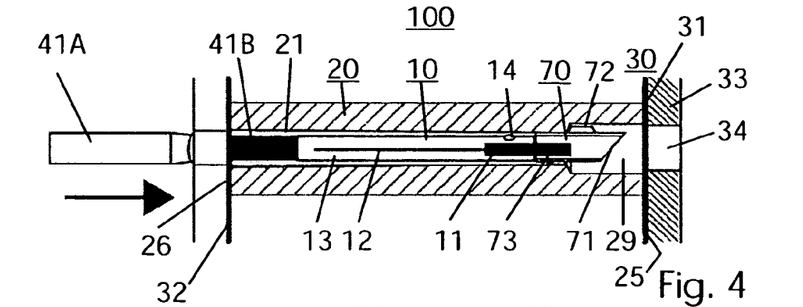
FIG 4. is a schematic sectional illustration of a further embodiment of the sterile-goods container according to the invention being provided with a mandrel.

A second embodiment of a container 100 according to the invention is illustrated in a closed condition in FIG. 4. This embodiment of the invention is adapted for guide tube acupuncture needles 10 which comprise a needle handle 11, needle section 12 and a guide tube 13. The needle handle 11 is fixed via a punctual adhesive joint 14 (see also FIG. 6) to the inner surface of the guide tube 13.

As with the embodiment according to FIG. 1, the receiving channel 21 in the container body 20 extends as a straight channel between the fronts and back sides 25, 26. However, with the second embodiment, a mandrel receptacle 29 is provided at the front side end of the receiving channel 21. The inner diameter of the mandrel receptacle 29 is greater than the inner diameter of the remaining receiving channel 21.

The receiving channel 21 is closed at the surfaces of the container body 20 with a cover 30 which comprises a paper or film cover 31, 32, e.g. made of Medical Paper as shown in FIG. 1. In FIG. 4, a so called pressure disc 33 is illustrated as an other part of the cover 30, wherein the pressure disk 33 has a through hole 34 according to the position of the receiving channel 21 or the mandrel receptacle 49. With the pressure disc 33, an unintended removal of the paper or film cover 31 can be avoided. The through hole 34 forms an additional guidance for the mandrel 70 and/or the sterile good.

With the embodiment of the invention shown in FIG. 4, furthermore a hollow mandrel 70 is provided which comprises a cutting area 71, a radial protrusion 72 and an elastic jacket 73. At the jacket 73, the inner diameter of the mandrel is variable. Before ejecting the acupuncture needle 10, mandrel 70 is positioned in the receiving channel 21 such that the cutting area 71 is directed towards the cover 31 and the jacket 73 is located in a pre-stressed condition in the receiving channel 21. The lateral protrusion 72 is positioned in the mandrel receptacle 29 of the receiving channel.

With the embodiment of the invention shown in FIG. 4, the actuating part 40 comprises two separate activating pins 41A, 41B. The first activating pin 41A is connected with a handle 42 or another mechanical component of the actuating part 40 as shown in FIG.1, while the second actuating pin 41B is positioned in the receiving channel 21. With this design, the guide tube 13 of the acupuncture needle 10 has the function of the pushing ram 21 shown in FIG. 1.

Figure 5:
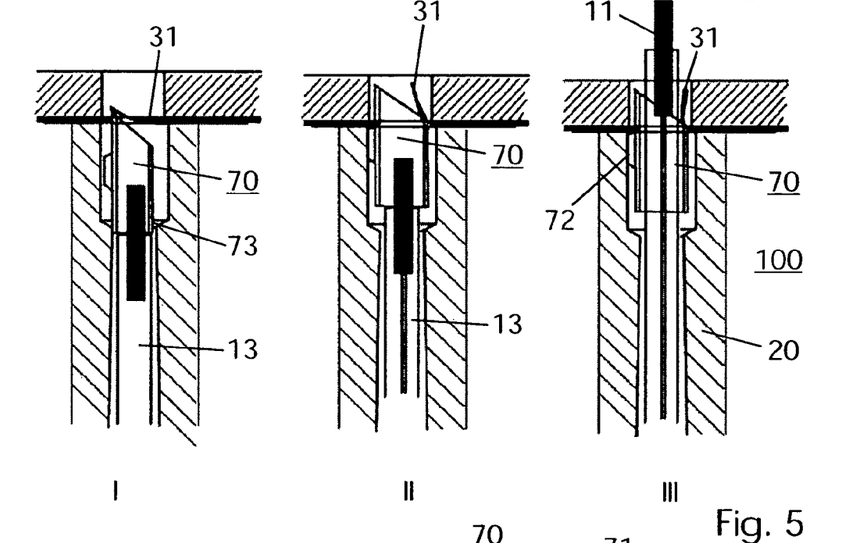
FIG. 5 depicts illustrations of various phases of ejecting the sterile-good from a sterile goods container of the invention according to the embodiment shown in FIG. 4.

When the actuating part 40 is actuated for ejecting the acupuncture needle 10 such that the actuating pins 41A, 41B are moved forward according to the direction of the arrow, the phases of releasing the acupuncture needle 10 result as shown in FIG. 5. In a first phase, the jacket 73 forms a rest for the guide tube 13 so that the mandrel 70 is moved towards the cover 31. The cover 31 is broken by the cutting area 71 (phase I).

With the further movement, the jacket 73 or (as shown) the whole mandrel 70 can be unwound (phase II, so that the inner diameter of the jacket 73 or the whole mandrel 70 is increased and a rest for the guide tube 13 is no longer provided by the jacket 73 or mandrel 70. During further feeding, the guide tube with the projecting needle handle 11 can be shifted through the hollow mandrel 70 (phase III), while the mandrel 70 with the protrusion 72 is retained by the residuals of cover 31. During the further progress, the needle handle 11 can be taken manually and drawn out of the container 100. The adhesive joint 16 is broken by a slight tilting of the needle handle 11 so that the guide tube 13 remains in container body 20.

Figure 6:
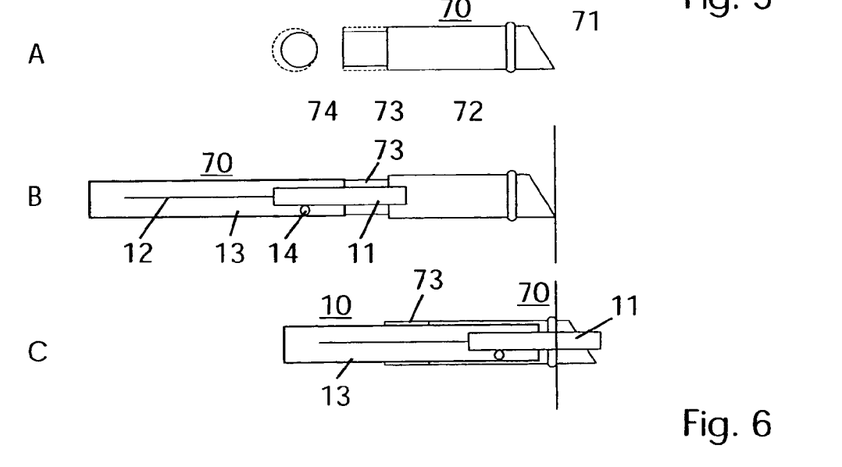
FIG. 6 depicts illustrations of details of a further embodiment of the sterile-goods container of the invention being provided with a mandrel.

FIG. 6 illustrates details of the Second embodiment of the invention wherein a mandrel 70 is provided in the container body like in FIG. 4. In chart A of FIG. 6, a sight view of mandrel 78 is illustrated with the cutting area 71, the protrusion 72 and the jacket 73. With this embodiment, the protrusion 72 is arranged cifcumferential around the mandrel 70. The jacket 73 comprises am elastic component having the shape of a cylinder with a longitudinal (axial) gap or overlapping which component has an integral connection with the remaining body of mandrel 70 at a short section (e.g., at 74) and for the rest a variable diameter. The diameter can be varied by bending the cylinder-shape wall of the jacket. In particular, the diameter can be increased from a pre-stressed, partially wound condition in the receiving channel 21 to a relaxed condition (shown with dashed line) in the mandrel receptacle 29. Chart B illustrates how the jacket 73 forms a stop for the guide tube 13 of acupuncture needles 10 in the pre-tensioned condition. Advantageously, no forces are exerted to the needle handle 11 connected via the adhesive joint 14 to the guide tube 13 and to the needle section 12 in this situation.

Chart C shows phase III of the ejecting movement of acupuncture needle 10 like in FIG. 5. In this situation, the guide tube 13 is protruding through the relaxed jacket 73 until the needle handle protrudes from mandrel 70 for manual taking-up.

Figure 7:
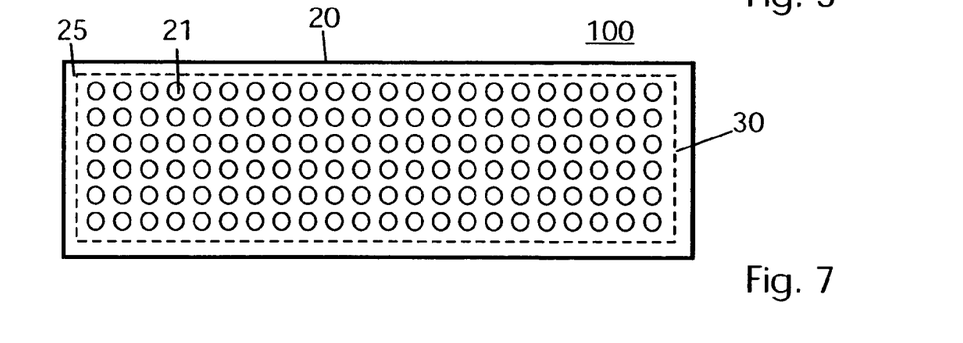
FIG. 7 depicts a schematic illustration of another embodiment of the sterile-goods container according to the invention with a plurality of receiving; channels.

FIG. 7 shows as another embodiment of the container 100 according to the invention with a container body 20 in which a plurality of receiving channels 21 are formed. A plan view of the front side 23 of a rectangular container body 20 is shown. The dashed line shows the extension of the Medical Paper used as cover 30. The receiving channels 21 are arranged such that they run straight and parallel to a side surface of the container body 20 so that their exit apertures (or points of intersection with a cross-sectional area of the container body 20) form a regular arrangement, e.g., of straight rows and columns. The container 100 according to FIG. 7 forms an acupuncture needle magazine from which the acupuncture needles can be released, for example, with an actuating part 40, as shown in FIGS. 1, 2 or 4.

The number of receiving channels 21 provided in the container body 20 is selected according to the dimensions of the goods to be stored and the specific application. In the case of acupuncture needles, this can, for example, be 50 to 100 or more.

Figure 8:
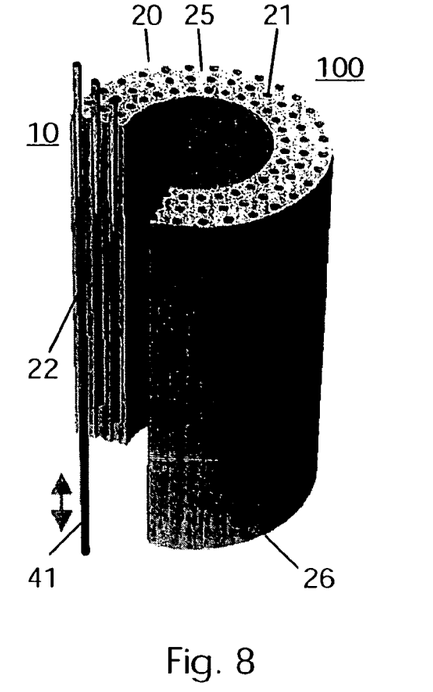
FIGS. 8-11 depict illustrations, of another embodiment of a sterile-goods container according to the invention with a plurality of receiving channels.

A modified embodiment of a container according to th,e invention for a plurality of individual acupuncture needles is illustrated in FIGS. 8 to 11. FIG. 8 shows the container body 20 in the form of a straight hollow cylinder in whose wall the receiving channels 21 are formed (illustration with cover). The receiving channels 21 run straight from the front side 25 to the back side 26 parallel to the cylinder axis. In each receiving channel 21 there is provided a pushing ram 22 similar to the application according to FIGS. 1 or 2 or a guide tube similar to the application according to FIG. 4. The displacement of the pushing ram 22 and the acupuncture needle 10 with the actuating pin 41 is illustrated in the left-hand part of FIG. 8.

Figure 9:
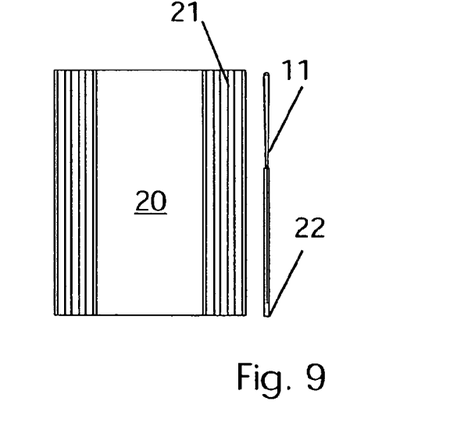
Figure 10:
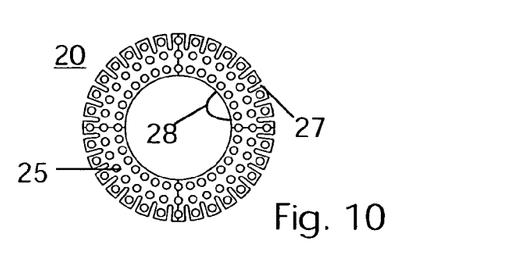

FIG. 9 shows a sectional view of the container body 20 with the receiving channels 21 and for illustration purposes separate from the container body 21, the pushing ram 22 with the acupuncture needle 10 whose needle section 12 projects into the pushing ram 22. FIG. 10 shows a plan view of the front side 25 of the container body 20 in whose surface slits 27 can be incorporated. The slits 27 can be advantageous for saving material and reducing weight and serve as engagement for an actuating device. FIG. 10 also illustrates a projection 28 which can be provided in the interior of the container body 20 and can serve as engagement for an actuating device (see FIGS. 12 and 13).

Figure 11:
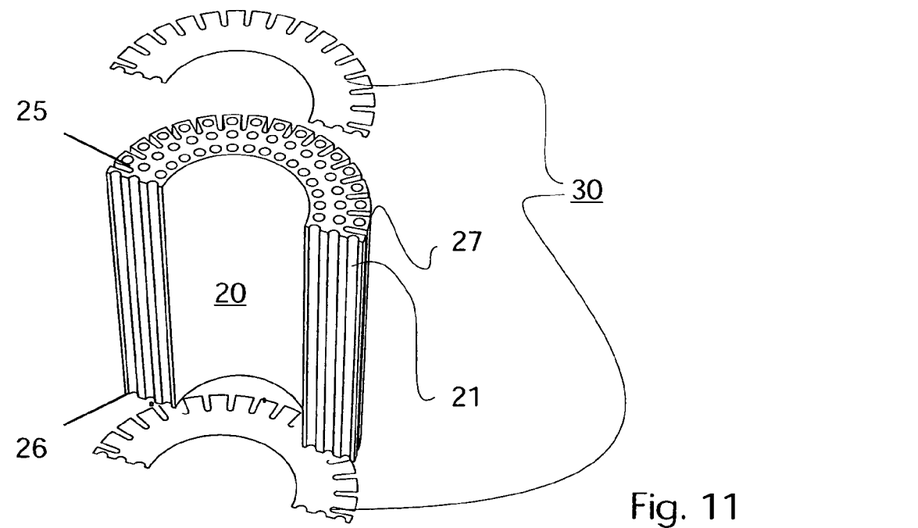

FIG. 11 illustrates the application of the cover 30 to the front and back sides 25, 26 of the container body 20 in a cutaway perspective view. Advantageously on both sides all the receiving channels 21 are respectively closed with a continuous ring of Medical Paper or a suitable covering film.

The container 100 according to the invention, for example in accordance with FIGS. 7 to 11 forms, according to a preferred embodiment of the invention, a magazine or dispensing module of a dispenser for sterile goods, especially for acupuncture needles. Two embodiments of the dispenser 200 according to the invention are illustrated, for example, in FIGS. 12 and 13.

Figures 12, 13:
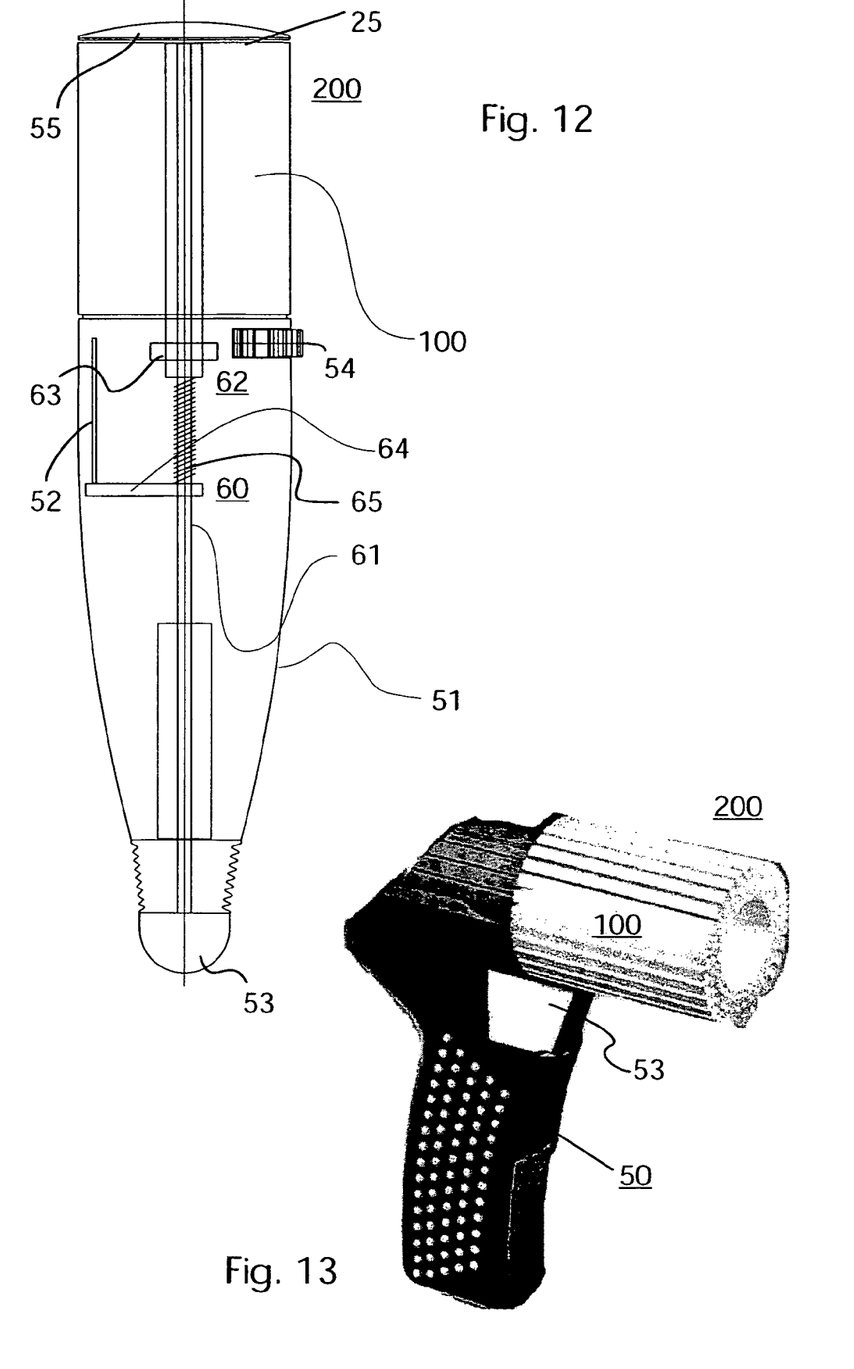
FIGS. 12-13 depict various embodiments of a sterile-goods dispenser according to the invention.

The dispenser 200 according to he invention comprises, according to FIG. 12, a container 100 for sterile goods and an actuating device 50, 60 for manual release of sterile goods from the container 100. The container 100 is for example set up as a cylindrical magazine according to FIGS. 8 to 11 to hold acupuncture needles.

The actuating device 50, 60 comprises a housing 51 in which an actuating pin 52 is arranged and a drive device 60 to drive the actuating pin 52. The drive device 60 comprises a feed rod 61 which leads from an actuating button 53 to an adjusting device 62. The adjusting device 62 is equipped with a click-stop device 63 to align the container 100 and a support 64 for the actuating pin 52. Said parts interact as follows.

The actuating pin 52 sits on the eccentrically adjustable support 64 which is adjustable with an adjusting wheel 54 in three positions corresponding to the three coaxial rings of receiving channels in the container 100 (see FIG. 10). On pressing the actuating button 53, the feed rod 61 executes a lifting movement with two steps. In the first step the container 100 rotates to a new position of a receiving channel. For this purpose the pushing movement of the feed rod 61 is converted with the latching device 63 into a rotary movement according to the grid size of the receiving channels in the container 100. In the second step the actuating pin 52 is displaced until it penetrates into the receiving channel in the container 100 and, in the manner described above, releases an acupuncture needle 10 at the front side 25 of the container 100. Under the action of the spring 65 the feed rod 61 is pulled back on releasing the actuating button 53. The reference number 55 refers to a protective cover which is removed during use of the dispenser 200.

Unlike the axial alignment of the feed rod 61 with the cylinder axis of the container 100 shown in FIG. 12, an axial deflection can also be provided as shown in FIG. 13. In this case, the drive device is accommodated in a housing 50 which forms a handle. The displacement of the actuating pin is accomplished using the actuating button 53. Alternatively the dispenser 200 can be fitted with an electrically operated drive device. The actuating device with the container is for example mounted on a wall in a laboratory and can be actuated using a servomotor.

The features of the invention disclosed in the preceding description, the drawings and the claim can be important both singly and in combination for the implementation of the invention in its various embodiments.

What is claimed is:

1. A container for holding a sterile good, comprising:
a container body with at least one continuous receiving channel having a cover at least at one end,
at least one acupuncture needle with a needle handle and a needle section, wherein the at least one acupuncture needle is arranged in the at least one receiving channel; and
at least one pushing ram which is displaceably arranged in at least one receiving channel, wherein a length of the at least one pushing ram is shorter than the channel length of the at least one receiving channel so that a cavity is formed in the receiving channel and the needle handle is arranged in the cavity wherein the pushing ram is shaped as a sleeve with an inner hole which receives the needle section, and the cavity is closed towards the outside by the cover.

2. The container according to claim 1, wherein said at least one pushing ram is shaped as a sleeve with an inner hole.

3. The container according to claim 1, wherein said at least one pushing ram comprises an external diameter that is equal to an internal diameter of said at least one receiving channel.

4. The container according to claim 1, wherein said at least one receiving channel has respectively one cover at both ends.

5. The container according to claim 1, wherein the cover is formed as a layer made of a material which is manually destructible by the sterile good.

6. The container according to claim 5, wherein the cover consists of sterile paper or film.

7. The container according to claim 2, wherein the diameter of the inner hole is less than the external diameter of the needle handle.

8. The container according to claim 1, which is equipped with an actuating part to displace said at least one pushing ram in the receiving channel.

9. The container according to claim 8, wherein the actuating part has an actuating pin, whose diameter is less than or equal to the channel internal diameter of the receiving channel.

10. The container according to claim 1, wherein a plurality of receiving channels are formed in the container body for accommodating a plurality of sterile goods.

11. The container according to claim 10, wherein the receiving channels run parallel from a front side to a back side of the container body.

12. The container according to claim 11, wherein the container body has the form of a circular cylinder between the front and back sides.

13. The container according to claim 12, wherein the receiving channels are arranged in the container body so that their points of intersection with a cross-sectional area of the container body form two or more coaxial circles.

14. The container according to claim 13, wherein the receiving channels in the container body are arranged in radial alignment.

15. The container according to claim 11, wherein the container body has the shape of a cuboid between the front and back sides.

16. The container according to claim 10, wherein on the front and back sides the cover for all the receiving channels is formed jointly respectively from one layer-shaped material.

17. A dispenser for sterile goods which has an actuating device and a container according to claim 1.

18. A method for supplying sterile good with a dispenser according to claim 17, wherein respectively one part of the sterile good is pushed out of the container, by moving the pushing ram using the actuating device in the corresponding receiving channel, until that part of the sterile good breaks through the cover and projects from the container body for subsequent usage.

19. The method according to claim 18, wherein respectively one acupuncture needle with a needle handle and a needle section is pushed out of the container respectively as sterile good until the needle handle breaks through the cover and projects from the container body.

\* \* \* \* \*